United States Patent [19]
Suzuki et al.

[11] Patent Number: 5,640,018
[45] Date of Patent: Jun. 17, 1997

[54] IMAGE DETECTING DEVICE AND MEDICAL X-RAY IMAGING APPARATUS

[75] Inventors: Masakazu Suzuki; Keisuke Mori; Akifumi Tachibana; Kazunari Matoba, all of Kyoto; Hitoshi Asai; Kazuhisa Miyaguchi, both of Hamamatsu; Toshitaka Takeguchi, Shizuoka, all of Japan

[73] Assignees: J. Morita Manufacturing Corporation, Kyoto; Hamamatsu Photonics Kabushiki Kaisha, Shizuoka, both of Japan

[21] Appl. No.: 598,441

[22] Filed: Feb. 8, 1996

[30] Foreign Application Priority Data

Feb. 9, 1995 [JP] Japan ................... 7-022147

[51] Int. Cl.$^6$ .................. G01N 23/04; A61B 6/14; G01T 1/20
[52] U.S. Cl. ...................... 250/368; 250/487.1
[58] Field of Search ........................ 250/368, 369, 250/487.1; 378/98.3

[56] References Cited

U.S. PATENT DOCUMENTS

| 5,138,166 | 8/1992 | Makino et al. | 250/368 |
| 5,461,233 | 10/1995 | Yamamoto et al. | 250/368 |

FOREIGN PATENT DOCUMENTS

| 2-29329 | 6/1990 | Japan . |
| 3-259569 | 11/1991 | Japan . |
| 4-80507 | 7/1992 | Japan . |

Primary Examiner—David P. Porta
Assistant Examiner—Richard Hanig
Attorney, Agent, or Firm—Koda and Androlia

[57] ABSTRACT

Images are to be satisfactorily continued even at joints of image regions.

The surface of a fluorescent screen on which an X-ray image is to be formed is partitioned in the longitudinal direction of a slit, into image regions. From the image regions, image information is guided to CCD imaging elements by optical fiber bundles. Boundaries of the image regions are formed so as to be inclined with respect to the longitudinal direction of a slit.

7 Claims, 5 Drawing Sheets

IMAGE DETECTING DEVICE AND MEDICAL X-RAY IMAGING APPARATUS

BACKGROUND OF THE INVENTION

1. Field of the Invention

The present invention relates to an image detecting device which is preferably used in a medical radiological diagnosis apparatus such as a dental X-ray panoramic tomography imaging apparatus, or an industrial nondestructive inspection apparatus, and also to a medical X-ray imaging apparatus using the image detecting device.

2. Description of the Related Art

In a dental X-ray panoramic tomography imaging apparatus, conventionally, an X-ray image which passes through a long and narrow slit and moves in a direction perpendicular to the longitudinal direction of the slit is taken while changing the light-receiving position in accordance with the movement of the image, as disclosed in, for example, Japanese Examined Patent Publication JP-B2 2-229329 (1990), and Japanese Unexamined Utility Model Publication JPU 4-80507 (1992). Japanese Unexamined Patent Publication JPA 3-259569 (1991) discloses a configuration in which a plurality of X-ray detecting elements are arranged in a staggered pattern and the arrangement pitch of light receiving elements is matched so as to receive X-ray fan beams. In the prior aft disclosed in JP-B2 2-29329, the imaging process is conducted by using a single X-ray image sensor. In the prior aft disclosed in JPU 4-80507, an X-ray image is formed on a scintillator using a fluorescent screen, and the image converted to visible light is guided by optical fiber bundles to a plurality of CCD image detecting elements, where the X-ray image is detected. The fluorescent face of the scintillator is partitioned into plural regions arranged in the longitudinal direction of the slit. An end face of each optical fiber bundle is joined to the regions and the CCD image detecting elements are disposed on the other end face of the optical fiber bundles, respectively.

FIG. 7 shows the configuration for detecting an X-ray image which is disclosed in JPU 4-80507. The fluorescent screen 1 constituting the scintillator converts incident X-rays into visible light. The slit for the X-ray panoramic tomography imaging has a long and narrow shape of, for example, 6 mm×150 mm, and practical CCD image detecting devices have a length of about 50 mm. Consequently, the surface of the fluorescent screen 1 is partitioned into three image regions 2, 3, and 4 which are arranged in the longitudinal direction of the slit. The CCD image detecting elements 8, 9, and 10 detect the image from the image regions 2, 3, and 4 through the optical fiber bundles 5, 6, and 7, respectively.

In the prior art disclosed in JPA 2-29329, since the single X-ray imaging element is used, it is difficult to take an image of a large slit, or the like. In the prior art disclosed in JPA 3-259,569, the plural X-ray imaging elements are arranged in a staggered pattern, and hence images detected by adjacent X-ray imaging elements are shifted in position and time from each other. Even when the images are subjected to an electrical signal processing, therefore, it is difficult to accurately reproduce the image.

In the prior art disclosed in JPU 4-80507, it is possible to take an image of the longitudinally elongating image region. However, since the boundaries of the image regions which are obtained by partitioning the fluorescent screen are formed in the image moving direction, images positioned in the boundaries cannot be sufficiently detected.

As shown in FIG. 8, each of the optical fiber bundles 5, 6, and 7 is formed by bundling a plurality of optical fibers 11. The end faces in the axial direction of each optical fiber 11 can be polished and aligned. When a side face of the optical fiber bundle 5, 6, or 7 is polished in a bundled state, however, some of the optical fibers 11 may be broken. Therefore, the optical fiber bundles 5, 6, and 7 cannot be subjected to a polishing process, and remain in a bundled state.

As a result, as shown in FIG. 9, each side face of the optical fiber bundle 5, 6, or 7 is not always in a perfectly aligned state, and inevitably has a somewhat rugged face. In the boundaries of the image regions 2, 3, and 4 where such optical fiber bundles 5, 6, and 7 are adjacent to each other, a gap 12 is often formed, so that the detection of an image 15 passing through the gap 12 is more difficult than that of images 13 and 14 passing through normal regions.

The diameter of each optical fiber 11 is smaller than the size of a light receiving element of the CCD image detecting elements 8, 9, and 10, so that plural optical fibers 11 correspond to one light receiving element. Therefore, the gap 12 is not formed when all the optical fibers 11 are initially bundled so as to conform to the fluorescent screen 1 shown in FIG. 7, and then divided into the optical fiber bundles 5, 6, and 7 in accordance with the image regions 2, 3, and 4 so as to be respectively distributed to the CCD image detecting elements 8, 9, and 10. However, it is impossible to cleanly divide the optical fibers 11 without damaging the optical fibers because the optical fibers are very thin. When some of the optical fibers 11 are once damaged, images in the vicinity of the boundaries of the image regions 2, 3, and 4 cannot be detected.

SUMMARY OF THE INVENTION

It is an object of the invention to provide an image detecting device in which an image region is partitioned into plural sections and images can be satisfactorily detected even in the boundaries, and a medical X-ray imaging apparatus using the image detecting device.

In the invention, the image detecting device is a device in which an image incident face is partitioned into a plurality of regions, and the regions are individually guided to imaging elements by optical fiber bundles, thereby detecting an image which relatively moves, wherein the image incident face is partitioned into a plurality of regions which are continuous in a direction crossing a moving direction of the image, the boundary of the region is set to be inclined with respect to the moving direction of the image, and the imaging element has a plurality of light receiving elements respectively corresponding to pixels which are arranged in a matrix form in the moving direction of the image and a direction perpendicular to the moving direction of the image.

In the invention, in the image incident face, the wavelength of the image to be formed is converted into a wavelength which can be detected by the imaging elements.

In the invention, the image detecting device is a device in which an image incident face is partitioned into a plurality of regions, and the regions are individually guided to imaging elements by optical fiber bundles, thereby detecting an image which relatively moves, wherein the regions of the image incident face which are partitioned are continuous in a direction crossing a moving direction of the image, the optical fiber bundles which individually guide the regions to the imaging elements are formed as units each having a generally parallelepiped shape, and the imaging elements are disposed on the back side of the image incident face and alternatingly arranged in both lateral sides with respect to a direction along which the regions are continuous.

In the invention, in portions in the vicinity of the boundaries of the regions, imaging elements corresponding to adjacent regions commonly have an effective light receiving face, and an image in the vicinity of a boundary of adjacent regions is duplicately taken by plural imaging elements corresponding to the regions.

In the invention, the imaging elements are CCD imaging elements, wherein an arrangement direction of vertical shift registers of the CCD imaging elements is set to be in the moving direction of the image, and a transfer clock signal which is supplied to the vertical shift registers is TDI-driven in accordance with the movement of the image.

In the invention, the medical X-ray imaging apparatus is an apparatus in which a medical X-ray image which has a long and narrow slit-like shape and moves in a direction perpendicular to a longitudinal direction is formed on a fluorescent substance layer, the fluorescent substance layer is partitioned into a plurality of regions, and the regions are individually guided to imaging elements by optical fiber bundles, thereby taking the X-ray image, wherein a surface of the fluorescent substance layer is partitioned into a plurality of regions which are continuous in a longitudinal direction of the slit, the boundary of each region is set to be inclined with respect to the moving direction of a fluorescent image, and the imaging elements have a plurality of light receiving elements respectively corresponding to pixels which are arranged in a matrix form in the moving direction of the fluorescent image and a direction perpendicular to the moving direction.

In the invention, the medical X-ray imaging apparatus is an apparatus in which a medical X-ray image which has a long and narrow slit-like shape and moves in a direction perpendicular to a longitudinal direction is formed on a fluorescent substance layer, the fluorescent substance layer is partitioned into a plurality of regions, and the regions are individually guided to imaging elements by optical fiber bundles, thereby taking the X-ray image, wherein regions of an image incident face which are partitioned are continuous in a direction crossing a moving direction of the image, the optical fiber bundles which individually guide the regions to the imaging elements are formed as units each having a generally parallelepiped shape, and the imaging elements are disposed on the back side of the image incident face and alternatingly arranged in both lateral sides with respect to a direction along which the regions are continuous.

In the invention, in portions in the vicinity of the boundaries of the regions, imaging elements corresponding to adjacent regions commonly have an effective light receiving face, and an image in the vicinity of a boundary of adjacent regions is duplicately taken by plural imaging elements corresponding to the regions.

In the invention, the medical X-ray image is a dental panoramic tomographic image.

According to the invention, the image incident face is partitioned into a plurality of regions which are continuous in a direction crossing the moving direction of the image, but the boundaries of the regions are set to be inclined with respect to the moving direction of the image. Consequently, an image incident on a boundary passes the boundary as the image moves and then enters one region which is adjacent in the crossing direction, so that the image exists in the boundary for only a relatively short period. Therefore, there is no possibility that lacking portions of image data due to the boundaries are continuous in the moving direction. Even when it is difficult to sufficiently detect an image in a boundary by the imaging elements, the image which has passed the boundary can be sufficiently detected by one region so that the rate of causing a trouble in detection when the image moves is small. In other words, with respect to an image corresponding to a portion where the boundary is inclined, an image in the vicinity of the boundary can be sufficiently compensated by, for example, adding the outputs of adjacent imaging elements. As a result, joints of images in boundaries of regions are prevented from appearing.

According to the invention, in the image incident face, the wavelength of the image is converted into a wavelength which can be detected by the imaging elements. Therefore, a large image of radiation of various kinds, X-rays, or the like can be formed and the resulting image can be efficiently detected by a plurality of visible light imaging elements.

According to the invention, the optical fiber bundles have a generally parallelepiped shape and are formed as units, and the imaging elements are alternatingly arranged in both lateral sides with respect to a direction along which the regions of the image incident face are continuous. Since the optical fiber bundles are formed as units as described above, it is not required to conduct positioning of the arrangement of optical fibers constituting the optical fiber bundles, and hence the optical fiber bundles can be easily assembled. Since the imaging elements are alternatingly arranged in both lateral sides, the degree of freedom of arrangement can be obtained and the imaging elements are prevented from interfering with each other. Therefore, the imaging element can be assembled by using known imaging elements such as CCD sensors, and the compactness of the devices can be attained and productivity in their manufacture can be improved.

According to the invention, since an image in the vicinity of a boundary of regions is duplicately taken by plural imaging elements, a portion which is not imaged because of the existence of the boundary can be compensated, so that joints of images are prevented from appearing.

According to the invention, CCD imaging elements are used as the imaging elements, an arrangement direction of vertical shift registers of the CCD imaging elements is set to be in the moving direction of the image, and the vertical shift registers are TDI-driven. Therefore, receiving signals can be accumulated in accordance with the movement of the image, so that the tomography or the like can be efficiently conducted.

According to the invention, a medical X-ray image which has a long and narrow slit-like shape can be detected in a divided manner by the plurality of imaging elements. Consequently, an X-ray image of a large area can be obtained; and therefore, so that the image can be sufficiently used in diagnosis and treatment.

According to the invention, an image in the vicinity of a boundary of regions is duplicately taken by plural imaging elements. Therefore, a portion of an image which is not imaged because of the existence of the boundary can be compensated, so that a X-ray image which is excellent as a medical image can be obtained.

According to the invention, since a dental panoramic tomographic image is taken as the medical X-ray image, it is possible to sufficiently detect an image from a long slit which is difficult to be detected by a single imaging element.

As seen from the above, according to the invention, even when the image forming face is partitioned into plural regions, images can be taken in such a manner that the images are satisfactorily continuous at joints of the regions. Therefore, a large image can be efficiently detected.

According to the invention, in the image forming face, the wavelength of light is converted so that an image which can be detected by the imaging elements is obtained. Therefore, an image of radiation such as X-rays can be efficiently detected.

According to the invention, since an image in the vicinity of a boundary of regions is duplicately taken by plural imaging elements, a portion which is not imaged because of the existence of the boundary can be compensated, so that joints of images are prevented from appearing.

According to the invention, CCD imaging elements are used as the imaging elements, and an image which is caused to move by TDI-driving can be efficiently detected.

According to the invention, a medical X-ray image which is to be used in diagnosis and treatment can be taken by plural imaging elements without causing reduction of the image quality due to existence of joints. This allows a large X-ray image to be used in diagnosis and treatment so as to obtain a sufficient amount of information of a portion which is to be subjected to diagnosis.

According to the invention, X-ray dental panoramic tomography imaging can be conducted by using plural imaging elements, and hence a clear tomographic image can be obtained with focusing on a dental arch.

BRIEF DESCRIPTION OF THE DRAWINGS

Other and further objects, features, and advantages of the invention will be more explicit from the following detailed description taken with reference to the drawings wherein.

DETAILED DESCRIPTION OF THE PREFERRED EMBODIMENTS

Figure 1:
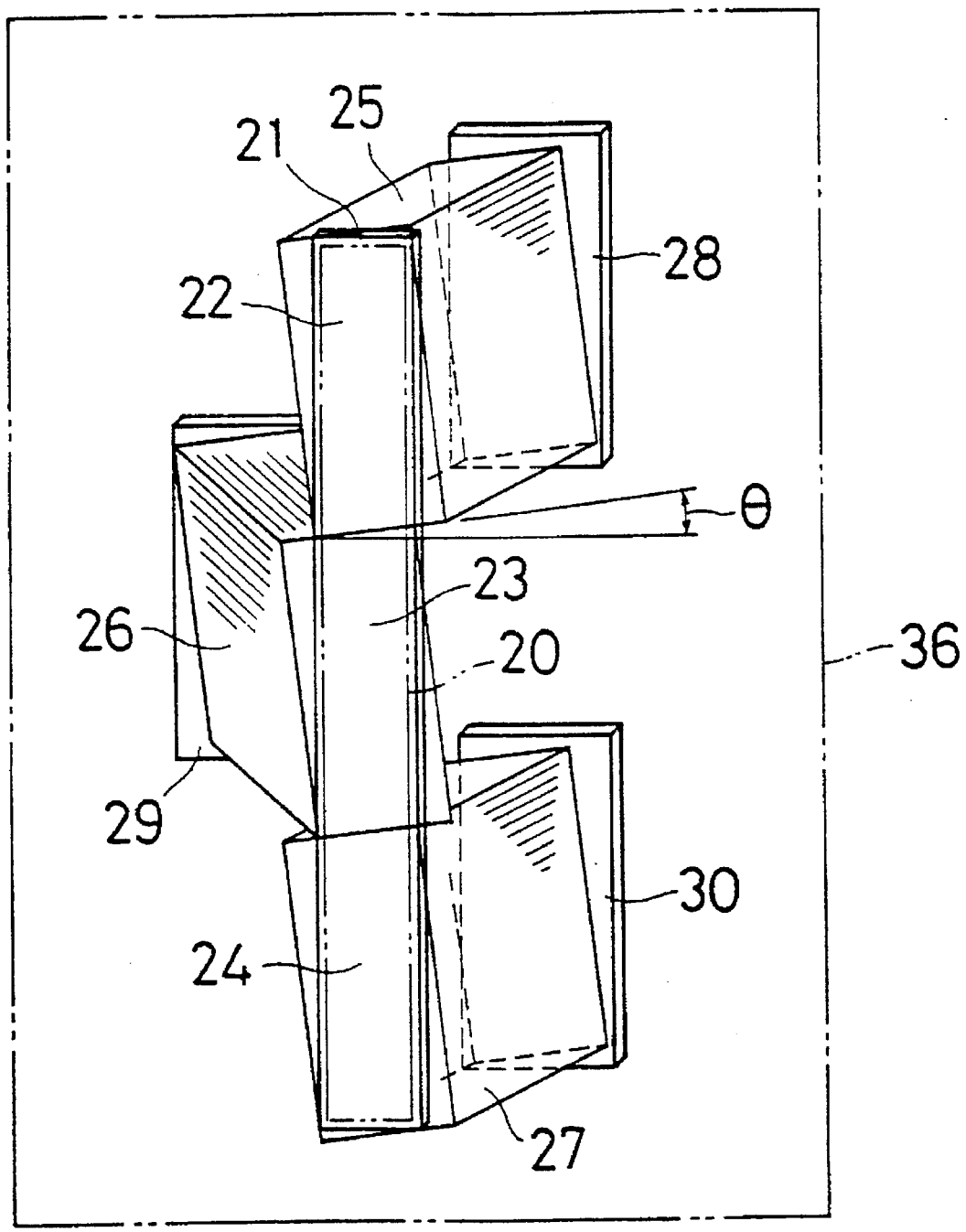
FIG. 1 is a perspective view of an image detecting device according to an embodiment of the invention.

Now referring to the drawings, preferred embodiments of the invention are described below.

Figure 2A:
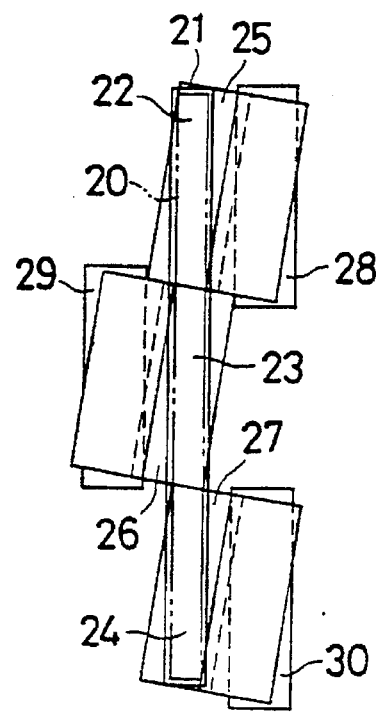
FIG. 2(A) is a front view of the embodiment of FIG. 1.
Figure 2B:
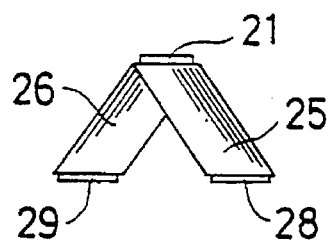
FIG. 2(B) is a plan view.
Figure 2C:
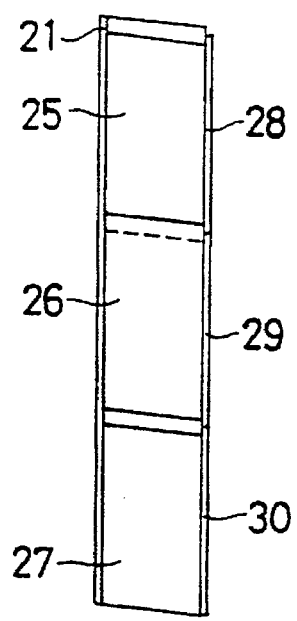
FIG. 2(C) is a side view.
Figure 3:
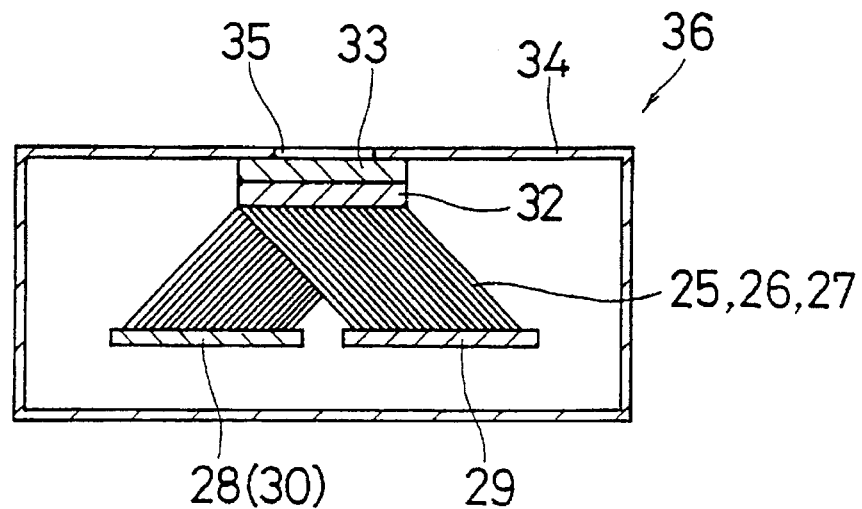
FIG. 3 is a section view showing an imaging head 36 having a fluorescent screen 32 in the embodiment of FIG. 1.

FIG. 1 is a perspective view of an image detecting device according to an embodiment of the invention, FIGS. 2(A), 2(B), and 2(C) are a front view of the embodiment, a plan view, and a side view, respectively, and FIG. 3 shows an imaging head 36. In the image detecting device, X-rays are made incident on the surface of the fluorescent screen 32 which is a fluorescent substance layer, so that an X-ray image 20 is formed as a fluorescent image in which the wavelength is converted by the fluorescent phenomenon. X-rays are incident on the fluorescent screen 32 through a slit which has a long and narrow shape of, for example, 150 mm in length and 6 mm in width. Consequently, also the fluorescent screen 32 has a long and narrow shape. The fluorescent screen 32 is partitioned into three image regions 22, 23, and 24 which are arranged in the longitudinal direction. Image information of the fluorescent image is divided and guided from the image regions 22, 23, and 24 to CCD imaging elements 28, 29, and 30 by optical fiber bundles 25, 26, and 27 which are formed as units each having a generally parallelepiped shape.

The fluorescent screen 32 is in close contact with the front faces of the optical fiber bundles 25, 26, and 27 so as to be optically joined thereto. When X-rays impinge on the fluorescent substance, the wavelength is converted so that an X-ray image can be visualized. The visualized image enters the CCD imaging elements 28, 29, and 30 through the optical fiber bundles 25, 26, and 27. In order to prevent the CCDs which detect visible light from being affected by external light, it is required to take a countermeasure such as that in which, as shown in FIG. 1, the whole of the detection system is housed in the imaging head 36 having light shielding properties.

As shown in FIG. 3, the fluorescent screen 32 is configured by a single plate-like member which is in close contact with the front faces of the optical fiber bundles 25, 26, and 27. Alternatively, the fluorescent screen 32 may be configured by, for example, a method in which a fluorescent substance is applied to the front faces of the optical fiber bundles 25, 26, and 27. A light shielding plate 33 is disposed on the front face of the fluorescent screen 32. Substrates having the CCD imaging elements 28, 29, and 30 are disposed on the rear faces of the optical fiber bundles 25, 26, and 27, respectively. The light shielding plate 33, the fluorescent screen 32, the optical fiber bundles 25, 26, and 27, and the CCD imaging elements 28 to 30 are housed in a light shielding box of the imaging head 36. The light shielding plate 33 is made of aluminum or plastics which is transparent to X-rays but opaque to visible light. The incident X-rays pass through the light shielding plate 33 and then impinge on the fluorescent screen 32 to be converted into visible light. The visible light is guided to the CCD imaging elements 28 to 30 via the optical fiber bundles 25, 26, and 27, thereby affording an image. As shown in FIGS. 1 and 2, preferably, the optical fiber bundles 25, 26, and 27 are disposed so as not to straightly approach the rear face of the fluorescent screen 32 but to be alternatingly arranged in both lateral sides of the rear face, in order to prevent the optical fiber bundles from being affected by the X-rays which have passed through the fluorescent screen 32.

When the optical fiber bundles 25, 26, and 27 are formed as units as described above, it is not required to conduct positioning of the arrangement of optical fibers constituting the optical fiber bundles, and hence the optical fiber bundles can be easily assembled. Since the CCD imaging elements 28, 29, and 30 are alternatingly arranged in both lateral sides, the degree of freedom of arrangement can be obtained and the imaging elements are prevented from interfering with each other. Therefore, the imaging elements can be assembled by using known CCD sensors, and the compactness of the devices can be attained and productivity in their manufacture can be improved.

The end faces of the optical fiber bundles 25, 26, and 27 have a rectangular shape, and are connected to the fluorescent screen 32 with being inclined with respect to the horizontal direction by an angle θ and shifted from each other. On the side of the CCD imaging elements 28, 29, and 30, the end faces are joined to the imaging elements with being inclined with respect to the vertical scanning direction by the same angle θ on the side of the fluorescent screen 32. Therefore, the width direction of the X-ray image 20 formed on the surface of the fluorescent screen 32 coincides with the vertical scanning direction of the CCD imaging elements 28, 29, and 30, and the longitudinal direction of the X-ray image 20 coincides with the horizontal scanning direction. On the surfaces of the CCD imaging elements 28, 29, and 30, the optical fiber bundles 25, 26, and 27 fail to cover the whole of the light receiving face. Therefore, it is preferable to leave the light receiving face open, particularly in each of the both ends in the horizontal scanning direction. Preferably, the open surfaces of the light receiving face are shielded from light.

In this way, an image in the vicinity of each boundary of the regions 22, 23, and 24 is duplicately taken by plural imaging elements. Consequently, a portion which is not imaged because of the existence of the boundary can be compensated, so that joints of images are prevented from appearing.

Figure 4:
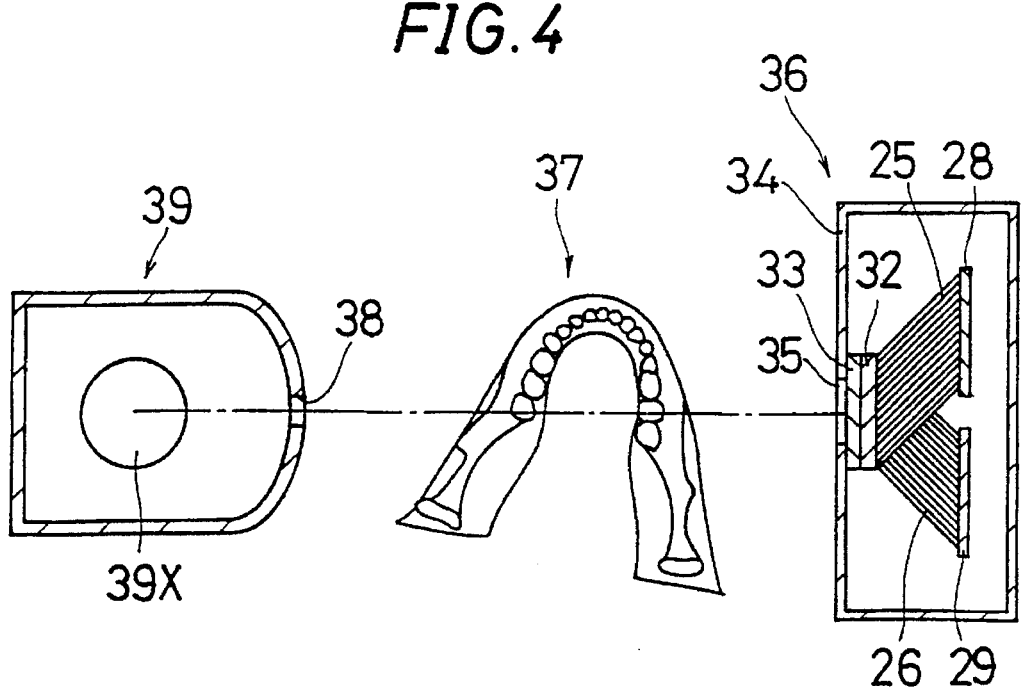
FIG. 4 is a simplified plan view of an X-ray panoramic tomography imaging apparatus according to another embodiment of the invention.

FIG. 4 shows the configuration in a plan view of a dental X-ray panoramic imaging apparatus of another embodiment of the invention. An X-ray image is detected by using the image detecting device of the embodiment of FIG. 1. The front portion of the light shielding plate 33 is covered by a shielding plate 34 which is opaque to X-rays. A slit 35 which vertically elongates and has a long and narrow shape is opened in the shielding plate 34. A tomographic image of a jaw 37 which is to be imaged is incident on the thus-configured imaging head 36. X-rays for imaging are generated by an X-ray tube 39X in an X-ray head 39 which serves as an X-ray source and has a slit 38. In the dental X-ray panoramic imaging apparatus, the slit 35 must have a length which approximately corresponds to the thickness of the jaw 37. By contrast, in order to obtain a clear tomographic image, the slit must have a small width. In order to subject the whole periphery of the jaw 37 to tomographic imagine, the imaging head 36 and the X-ray head 39 must be revolved around the jaw 37 while the heads are opposed to each other.

Figure 5:
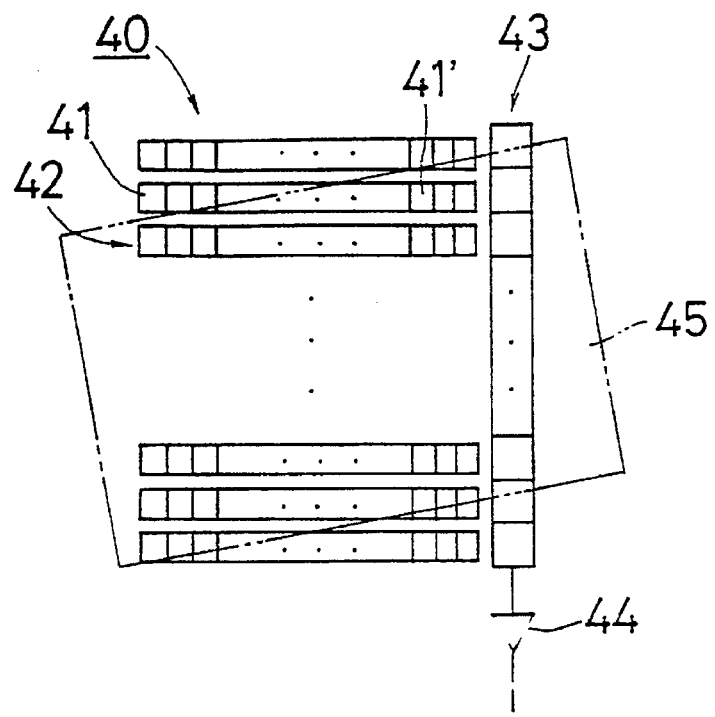
FIG. 5 is a simplified front view showing the configuration of a light receiving face of an FFT type CCD device which is used in the embodiments of FIGS. 1 and 4.

FIG. 5 shows the configuration of a full frame transfer (hereinafter, abbreviated as FFT) type CCD image sensor 40 which is preferably used as the CCD imaging elements 28, 29, and 30 of the embodiment of FIG. 4. The plural light receiving elements 41 of the FFT type image sensor 40 are arranged in a matrix form, in the vertical scanning direction which is substantially horizontal in the arrangement, and in the horizontal scanning direction Which is substantially vertical in the arrangement. The horizontal moving direction of the image is made coincident with the vertical scanning direction. Light incident on the light receiving elements 41 is converted into charges. The charges are then sequentially transferred by vertical shift registers 42 which are disposed substantially horizontally in an attached state, and in which the charge transfer direction is vertical. When the transfer timing is matched with the timing of the movement of the image in the vertical scanning direction, it is possible to focus on a specific tomographic image or the like. This principle is applied in the TDI method which is disclosed in, for example, Japanese Unexamined Patent Publication JPA 3-13080 (1991). In the embodiment, a light receiving region 45 to which the end face of the optical fiber bundle 25, 26, or 27 is connected and which has a rectangular shape is inclined with respect to the rectangle formed by the matrix of the light receiving elements 41, and hence there exist some light receiving elements 41 which are not in the light receiving region 45. In order to prevent the image detection from being disturbed, a light shielding process must be conducted on the surfaces of such light receiving elements 41.

Figures 6A, 6B, 6C:
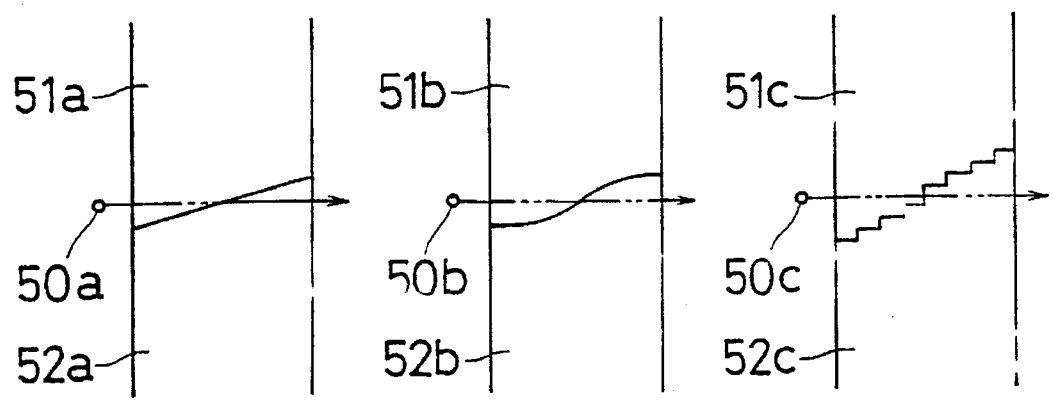
FIG. 6A, 6B, 6C are simplified front views showing the partition state of an image region in a further embodiment of the invention.
Figure 7:
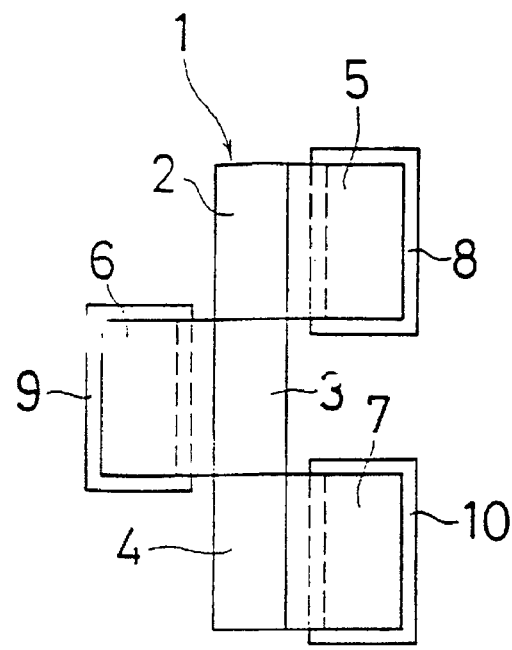
FIG. 7 is a simplified front view showing a method of partitioning an image region in the prior art.
Figure 8:
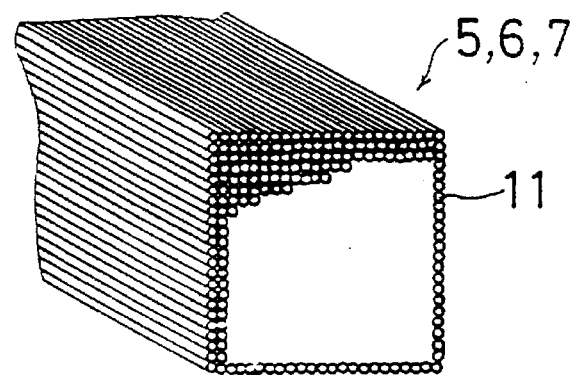
FIG. 8 is a partial perspective view showing the configuration of an optical fiber bundle.
Figure 9:
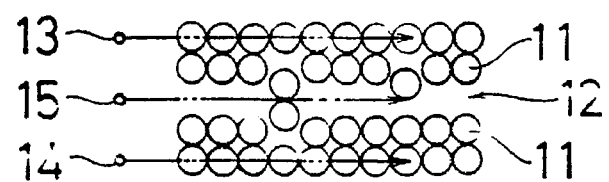
FIG. 9 is a partial enlarged view showing the state in the vicinity of a boundary of the image regions of FIG. 7 which is formed by the optical fiber bundle of FIG. 8.

FIG. 6 illustrates the fundamental concept of the partition of the light receiving face. In (A) of the figure, the boundary of regions 51a and 52a is a straight line which is inclined with respect to the moving direction of an image point 50a in the same manner as the embodiment of FIG. 1. When an image point 50b or 50c moves so as to cross a boundary for a moment, as shown in (B) and (C), boundaries of regions 51b and 52b, and 51c and 52c may have a curved shape or a step-like shape. The regions 51a, 51b, and 51c are assigned to FFT type CCD image sensors that are adjacent to and different from those to which the regions 52a, 52b, and 52c are assigned, respectively. Therefore, an image corresponding to the image point 50a, 50b, or 50c is obtained by adding outputs of adjacent FFT type CCD image sensors 40.

In the FFT type CCD image sensor 40 shown in FIG. 5, for example, light receiving elements 64 are arranged in the vertical scanning direction which corresponds to the width direction. Even when some of the light receiving elements 41 fail to detect an X-ray image in a boundary, the X-ray image can be sufficiently detected by the remaining light receiving elements 41'. The X-ray detecting device may be used also in the case where a simple scanning operation is done by using fan beams as disclosed in JPA 3-259569, and in the case where nondestructive inspection is industrially conducted, such as that where objects transported on a belt conveyor are continuously subjected to radioscopy. When the kind of the fluorescent substance of a fluorescent screen 21 is changed, an image of radiation other than X-rays can be detected. Alternatively, a moving image may not be processed by the imaging elements themselves, but once stored in a memory and then processed by a digital process as disclosed in JPA 2-29329. In the alternative, imaging elements of the type other than the FFT type CCD image sensor 40 may be used as the imaging elements. Examples of such imaging elements are a frame transfer (FT) type CCD image sensor, an interline transfer (IT) type CCD image sensor, and a frame interline transfer (FIT) type CCD image sensor.

The invention may be used in a wide variety of detections of a visible light image other than a detection of an X-ray image. In such a case, the light shielding plate 33 and the fluorescent screen 32 are not necessary, and only the optical fiber bundles and the imaging elements are required.

Preferably, each of the optical fibers constituting the optical fiber bundles 25, 26, and 27 is a single or so-called straight fiber in which the incident and outgoing ends are optically coupled with each other in a one-to-one relationship. According to this configuration, distortion can be reduced. Alternatively, optical fibers which are different in material, optical properties such as the refractive index, and diameter may be used.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. An image detecting device for detecting a relatively moving image comprising:

an image incident face partitioned into a plurality of regions that are continuous in a direction crossing a moving direction of the image, wherein the boundary of each region is set to be inclined with respect to the moving direction of the image;

imaging elements, each having a plurality of light receiving elements, which correspond to pixels that are arranged in a matrix form in the moving direction of the image and in a direction perpendicular thereto; and optical fiber bundles for individually guiding each region of the image incident face to an imaging element.

2. The image detecting device according to claim 1, wherein the wavelength of the image to be formed is converted into a wavelength which can be detected by the imaging element on the image incident face.

3. The image detecting device according to claim 1, wherein in portions in the vicinity of the boundary of each region, the imaging elements corresponding to adjacent regions commonly have an effective light receiving face, and an image in the vicinity of a boundary of the adjacent regions is duplicately taken by plural imaging elements corresponding to the regions.

4. The image detecting device according to claim 1, wherein the imaging element is a CCD imaging element wherein an arrangement direction of vertical shift registers of the element is set to be in the moving direction of the image, and a transfer clock signal which is supplied to be the vertical shift registers TDI driver in accordance with the movement of the image.

5. A medical X-ray imaging apparatus for taking an X-ray image which has a long and narrow slit-like shape and which moves in a direction perpendicular to a longitudinal direction, said apparatus comprising:

a fluorescent substance layer on which the X-ray image is formed, the layer including a surface thereof partitioned into a plurality of regions continuous in a longitudinal direction of the slit, wherein the boundary of each region is set to be inclined with respect to the moving direction of a fluorescence image;

imaging elements, each having a plurality of light receiving elements which correspond to pixels that are arranged in a matrix form in the moving direction of the fluorescence image and in a direction perpendicular thereto; and optical fiber bundles for individually guiding each region of the fluorescent substance layer to an imaging element.

6. The medical X-ray imaging apparatus according to claim 5, wherein in portions in the vicinity of the boundary of each region, the imaging elements corresponding to adjacent regions commonly have an effective light receiving face, and an image in the vicinity of a boundary of the adjacent regions is duplicately taken by plural imaging elements corresponding to the regions.

7. The medical X-ray imaging apparatus according to claim 5, wherein the X-ray image is a dental panoramic tomographic image.

* * * * *